United States Patent [19]

Keshaviah et al.

[11] Patent Number: 5,518,623

[45] Date of Patent: May 21, 1996

[54] HEMODIALYSIS MONITORING SYSTEM FOR HEMODIALYSIS MACHINES

[75] Inventors: Prakash Keshaviah, Plymouth, Minn.; James P. Ebben, Hudson, Wis.; Paul F. Emerson, Minnetonka; David A. Luhring, Savage, both of Minn.

[73] Assignee: Baxter International Inc., Deerfield, Ill.

[21] Appl. No.: 239,936

[22] Filed: May 9, 1994

Related U.S. Application Data

[63] Continuation of Ser. No. 959,922, Oct. 19, 1992, abandoned.

[51] Int. Cl.$^6$ ............................. B01D 61/30; B01D 61/32
[52] U.S. Cl. ..................... 210/646; 210/96.2; 210/739; 364/413.02; 422/68.1; 436/108; 604/4; 604/5
[58] Field of Search ................ 210/85, 93, 96.2, 210/143, 321.71, 646, 647, 739, 746, 929; 204/153.14, 406; 604/4, 5, 6, 28, 29; 436/108; 364/413.01, 413.02, 413.07; 422/68.1

[56] References Cited

U.S. PATENT DOCUMENTS

| | | | |
|---|---|---|---|
| 3,802,562 | 4/1974 | Kozlov et al. | 210/96.2 |
| 4,112,768 | 9/1978 | Holland et al. | 73/422 R |
| 4,244,787 | 1/1981 | Klein et al. | 204/153.14 |
| 4,370,983 | 2/1983 | Lichtenstein | 210/929 |
| 4,508,622 | 4/1985 | Polaschegg et al. | 210/96.2 |
| 4,668,400 | 5/1987 | Veech | 210/96.2 |
| 4,686,479 | 8/1987 | Young et al. | 324/439 |
| 4,722,798 | 2/1988 | Goss | 210/646 |
| 4,955,857 | 9/1990 | Shettigar | 604/3 |
| 5,024,756 | 6/1991 | Sternby | 210/93 |
| 5,100,554 | 3/1992 | Polaschegg | 210/647 |
| 5,110,477 | 5/1992 | Howard et al. | 210/647 |
| 5,142,271 | 8/1992 | Bailey et al. | 340/606 |
| 5,230,702 | 7/1993 | Lindsay et al. | 604/4 |
| 5,247,434 | 9/1993 | Peterson et al. | 364/413.02 |

FOREIGN PATENT DOCUMENTS

| | | |
|---|---|---|
| 80109767 | 8/1992 | |
| 0437789A2 | 7/1991 | European Pat. Off. . |
| 0504772A2 | 9/1992 | European Pat. Off. . |
| 0495412A1 | 10/1992 | European Pat. Off. . |
| 3436748A1 | 7/1985 | Germany . |

OTHER PUBLICATIONS

Laurie J. Garred, et al., "Artificial Organs", vol. 16, No. 3, pp. 248–255, 1992; and Abstracts vol. 15, p. 285 No. 4, 1991.

Thomas A. Depner, "Quantitation of Dialysis", vol. 5, No. 2, pp. 147–154, 1992.

E. Klein and J. G. Montalvo, Jr., "International Journal of Artificial Organs", vol. 1, No. 3 pp. 116–122 and No. 4, pp. 175–180, 1978.

"Abstracts of the XII Annual CAPD Conference", vol. 12, Supplement 1, 1992.

*Primary Examiner*—Joseph W. Drodge
*Attorney, Agent, or Firm*—Thomas S. Borecki; Charles R. Mattenson; Anibal Jose Cortina

[57] ABSTRACT

An improved on-line real time hemodialysis monitoring system for hemodialysis treatment. The hemodialysis monitoring system quantitates the rate and amount of a constituent, such as urea, removed during the hemodialysis treatment by measuring the constituent concentrations as a function of time in the spent dialysate effluent from a hemodialysis machine. A quantity of the spent dialysate effluent is removed from the dialysate effluent waste line periodically for testing. A urea concentration time profile can be analyzed to determined the urea removal, KT/V, URR, SRI and normalized protein catabolic rate (nPCR) indices. The hemodialysis monitoring system preferably can obtain a dialysate sample equilibrated with the blood prior to the start of a hemodialysis treatment. The hemodialysis monitoring system includes a two pool analysis for taking into account the constituent concentration differences in the extracellular and intracellular spaces in the hemodialysis patient during the hemodialysis treatment.

48 Claims, 4 Drawing Sheets

HEMODIALYSIS MONITORING SYSTEM FOR HEMODIALYSIS MACHINES

This is a continuation of application Ser. No. 07/959,922, filed Oct. 13, 1992, now abandoned.

FIELD OF THE INVENTION

The present invention relates generally to hemodialysis machines, and more particularly is directed to an improved system for on line real time monitoring of the effectiveness of the hemodialysis treatment.

BACKGROUND OF THE INVENTION

The use of dialyzer cartridges with hemodialysis machines to remove blood-borne toxins and by-products of metabolism has been conventional for many years. Typically, such a cartridge contains essentially a pair of chambers separated by a semipermeable membrane. Blood is perfused through the first chamber and returned to the patient. The dialysate solution is simultaneously circulated in the opposite direction through the second chamber. A concentration gradient thereby is established which causes waste products carded in the blood to migrate through the semipermeable membrane and into the dialysate solution to form the dialysate effluent.

The principle of hemodialysis has been refined extensively. A number of semipermeable hollow fiber membranes are now utilized in dialyzer cartridges to greatly increase the total membrane surface area to facilitate diffusion across the membrane structure. The hollow fiber membranes include a variety of materials including, for example, cellulose acetate, cellulose triacetate, polyacrylonitrile, polysulfone, and regenerated cellulose, the latter being most commonly used.

One of the most basic considerations in treating a patient with hemodialysis revolves around treatment adequacy. For instance, how long should a given patient be dialyzed on a given day. A number of medically adverse effects may result from an inadvertent failure to sufficiently dialyze the patient. At the present time, the average dialysis patient has a life expectancy of only about five years. One reason these patients tend to have a short life expectancy is the deleterious effect of a chronic buildup of various toxins that either are not eliminated at all, i.e. do not pass through the hollow fibers, or are not sufficiently reduced to nontoxic levels. The identity of many of these supposed toxins is not known, although those species known to be eliminated in urine, such as urea, creatinine, phosphate, hydrogen ions, etc. are associated with serious medical consequences when permitted to accumulate in excess of normal levels.

A number of factors can have a substantial effect on treatment adequacy. For example, it is common practice in the field of hemodialysis to reuse the dialysis cartridges. There is technology available for cleaning, disinfecting, or sterilizing used dialysis cartridges, for example, as illustrated in U.S. Pat. No. 4,695,385. Eventually, however, an individual cartridge must be discarded because it loses its dialyzing competency. At the present time, the competency of dialyzers is difficult to assess and therefore often is not rigorously monitored, and a dialyzer cartridge is often not discarded until it visually appears unclean after recleaning, or when fiber bundle volumes or ultrafiltration rates are reduced below a predetermined threshold. It now is known that severe dialyzer dysfunction can occur even when appearance, fiber bundle volume and ultrafiltration rates are normal, as reported by Delmez et al., "Severe dialyzer dysfunction during reuse," *Kidney International*, 35:244 (1989). It is also known that dialyzer competency can not be accurately predicted by the age of the dialyzer cartridge or the number of uses.

Notwithstanding the condition of the dialyzer, one measure of adequacy of dialysis for the individual patient during a given treatment is calculated from the following equation:

$$KT/V \geq 1.0$$

V is an expression of the volume of distribution of urea which is approximately equal to total body fluid volume. V is derived for each individual patient from data such as height, weight and sex. K is the urea clearance of the particular dialyzer in use in milliliters (ml) of blood cleared of urea each minute. T is the treatment time. K is obtained from the typical product insert enclosed with a case of dialyzers and contains a graph of urea clearance versus blood flow rate obtained by random testing of a sample of dialyzers from a particular manufacturing lot. Upon incorporating these values into the above equation, the minimum treatment time can be calculated for a given KT/V value. Other parameters that may be varied to achieve adequate dialysis include blood flow rate, dialysis solution flow rate, dialyzer competency, and temperature.

It has been determined empirically that KT/V values of about 0.8 or greater are associated with low levels of morbidity. See Gotch, L. A., Sargent, J. A. *Kidney International*, 28:526–537, 1985. Even with the use of new dialyzers there is some risk that a unit selected from a particular lot will have a significantly lower K value than the value indicated in the product insert. The patient receiving treatment from such a dialyzer is therefore at risk of being under-dialyzed. The likelihood of under-dialysis increases upon reuse of the dialyzer cartridge because of the definite but unquantified loss of dialyzer competence with each successive use. Underdialysis also may occur because of incompetency of access to the patient's circulation. Because of incompetency of the patient's blood access, desired blood flow rates may not be achieved which also can result in underdialysis.

Other parameters than KT/V have also been determined to assess the adequacy of dialysis. Among these are the Urea Reduction Ratio (URR) and Solute Removal Index (SRI). URR is defined as $1-(C_B)_{pre}/(C_B)_{post}$. A good dialysis treatment will have a URR near one (1) while a poor dialysis treatment will have a URR near zero (0). Unfortunately URR does not take into account generation of urea during dialysis, ultrafiltration, or the two pool nature of removal. Consequently SRI has been proposed as a generalized version of URR which does account for these effects. SRI is defined as the amount of urea removed during a treatment as a fraction of the total body store. Like URR, a good dialysis treatment will have an SRI value near one (1) while a poor dialysis treatment will have an SRI near zero (0). Potentially SRI (unlike KT/V) can indicate the adequacy of a dialysis treatment irrespective of modality (i.e. peritoneal or hemodialysis) and intermittence. Neither URR or SRI however, have been validated as extensively as KT/V as measures of dialysis adequacy.

Although the KT/V, URR and SRI indices are indicative of urea removal and appear to correlate to therapy failure, that is not tantamount to saying that urea is a toxic metabolite. There is early literature to suggest that urea is not toxic, per se. However, urea is a major metabolite of protein catabolism and serves as a convenient marker to monitor treatment adequacy.

Urea has a molecular weight of 60 daltons while some of the other protein catabolites may be much larger. It has, therefore, become a subject of controversy whether the relationship between KT/V and morbidity established with the tighter cellulosic membranes is applicable to the more open membranes used for hemofiltration and high flux hemodialysis or to the natural peritoneal membrane.

There is a considerable body of literature on the urea kinetic model. Computer programs, programmable calculators and time-shared computer services have been determined to make urea kinetics more accessible to the dialysis clinician. It has recently been shown (Lindsay, et at, 1989) that KT/V values of less than 0.8 may be associated with a low dietary protein intake that is intractable to nutritional counseling. However, increasing the KT/V to 1.0 or higher, in conjunction with nutritional counseling, is effective in improving dietary protein intake. As low dietary protein intake may be associated with increased morbidity, monitoring of the KT/V and nPCR are useful adjuncts to other clinical assessments of the dialysis patient.

Traditional urea kinetics entails numerous measurements and is considered mathematically complex by dialysis clinicians. The various measurements required for accurate kinetic measurements are summarized in Table 1.

TABLE 1

MEASUREMENTS REQUIRED FOR UREA KINETIC CALCULATIONS

Pre dialysis BUN ($C_1$)
Post dialysis BUN ($C_2$)
Pre dialysis BUN for next dialysis ($C_3$)
Dialyzer clearance (K)
  Blood flow rate
  Arterial BUN
  Venous BUN
  Dialysate flow rate (effluent) ($Q_{Do}$)
Access recirculation
  Peripheral BUN
Residual renal function
  Urine volume
  Urine concentration
Dialysis duration ($t_d$)
Off dialysis duration ($t_{od}$)
Ultrafiltration rate
Weight gain between dialyses Each of these measurements is associated with finite error and the cumulative effect of these errors may lead to unrealistic urea kinetic parameters.

Prior art hemodialysis machines have not had the capability of on-line monitoring of the hemodialysis treatment. Further, the prior art techniques generally have required the taking of blood samples from the hemodialysis patient.

It thus would be desirable to provide a non-invasive on-line real time monitoring of the hemodialysis treatment while the patient is attached to the hemodialysis machine. The treatment when based on urea kinetics preferably would require measurements of effluent dialysate concentrations and flow but not of blood samples. The treatment would yield as outputs the KT/V, URR and SRI indices of therapy adequacy, the urea removal and the normalized protein catabolic rate (nPCR) which then could be utilized to assess dietary compliance and adequacy of treatment in real time.

SUMMARY OF THE INVENTION

The present invention is directed to an improved on-line real time hemodialysis monitoring method and system for hemodialysis machines. The hemodialysis monitoring system quantitates the rate and amount of urea removed during the hemodialysis treatment by measuring the urea concentration in the spent dialysate effluent as a function of time. The dialysate effluent line from the hemodialysis machine is sampled periodically to remove a small volume of the spent dialysate effluent when a sufficient fluid flow is sensed. The urea concentration-time profile is determined and analyzed to determined the urea removal, KT/V, URR and normalized protein catabolic rate (nPCR). The hemodialysis monitoring system and urea monitor configuration can be changed to allow equilibrium of blood in the dialysate effluent prior to the start of and at the end of a hemodialysis treatment. The hemodialysis monitoring system also can include a two pool analysis taking into account the different degree of urea depletion from the extracellular and intracellular spaces in the hemodialysis patient during treatment. This allows the calculation of the solute removal index (SRI).

These and other features and advantages of the invention will be more readily apparent upon reading the following description of a preferred exemplified embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENTS

Figure 1:
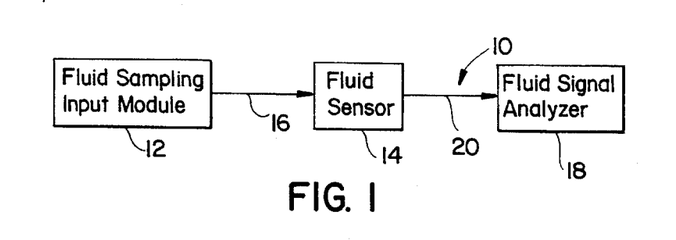
FIG. 1 is a block diagram of one embodiment of the hemodialysis monitoring system of the present invention.

Referring to FIG. 1, one embodiment of a hemodialysis monitoring system of the present invention is designated generally by the reference numeral 10. The monitor 10 includes an input module 12, which can in the preferred embodiment be a urea sensor or an appropriate sensor for sensing a different molecule or constituent to be cleared. The module 12 samples a volume of the dialysate effluent intermittently, as desired. The module 12 couples the dialysate sample volume to a sensor 14 via a line 16. The sensor 14 generates a signal which is proportional to the monitored constituent concentration and couples that signal to a constituent signal analyzer 18 via a line 20.

The module 12 can be any type of sampling device which is coupled, preferably permanently, to the dialysate effluent line (not illustrated). A preferred input module 12 is disclosed and described in copending application docket number DI-4354 (65889-108), entitled FLUID SAMPLING MODULE, filed concurrently herewith, which is incorporated herein by reference. The urea sensor 14 can be a sensor, such as described in U.S. Pat. No. 4,686,479, entitled APPARATUS AND CONTROL KIT FOR ANALYZING BLOOD SAMPLE VALUES INCLUDING HEMATOCRIT, which also is incorporated herein by reference. The liquid sample is contacted with a urea sensor that includes a urease layer associated with an electrode adapted to generate output in response to ammonium ions. The urease layer converts a portion of the urea in the sample to ammonium ions, and the ions contact the electrode to generate output related to the urea concentration in the sample.

The sensor 14 is described herein for example purposes, as a urea sensor. There are other approaches to urea sensing and any urea sensor that can measure urea concentration in the effluent dialysate line can be utilized for this purpose. The invention, therefore, is not specific to a particular type of urea sensor. Urea, however, is just one of a number of identifiable constituents generally related to uremia in a patient's blood, which can be utilized as a marker or measure of the effectiveness of the hemodialysis treatment, i.e. the removal of toxins. Such other constituents are, for example, creatinine, uric acid, phosphate, calcium, sodium, potassium, glucose, beta 2 microglobulin, among others. Other types of sensors also can be utilized in the hemodialysis monitoring system of the present invention, which sense the required fluid constituent(s) directly or indirectly.

There are also other approaches to the flow configuration of the urea sensor. The most direct configuration is location of the urea sensor in the effluent dialysate stream. Another direct configuration is taking the sample volume from the fluid stream and flowing the sample volume past the sensor. Other configurations could include:

1. Locating the sensor in the fresh inflow dialysate stream with effluent dialysate being pumped in, upstream of the sensor, in a flow injection mode.
2. Pumping inflow and outflow streams in the desired proportions for dilution past the urea sensor.
3. A flow injection scheme where a carrier buffer stream is pumped past the urea sensor with injection of effluent dialysate into this buffer stream.

Figure 2:
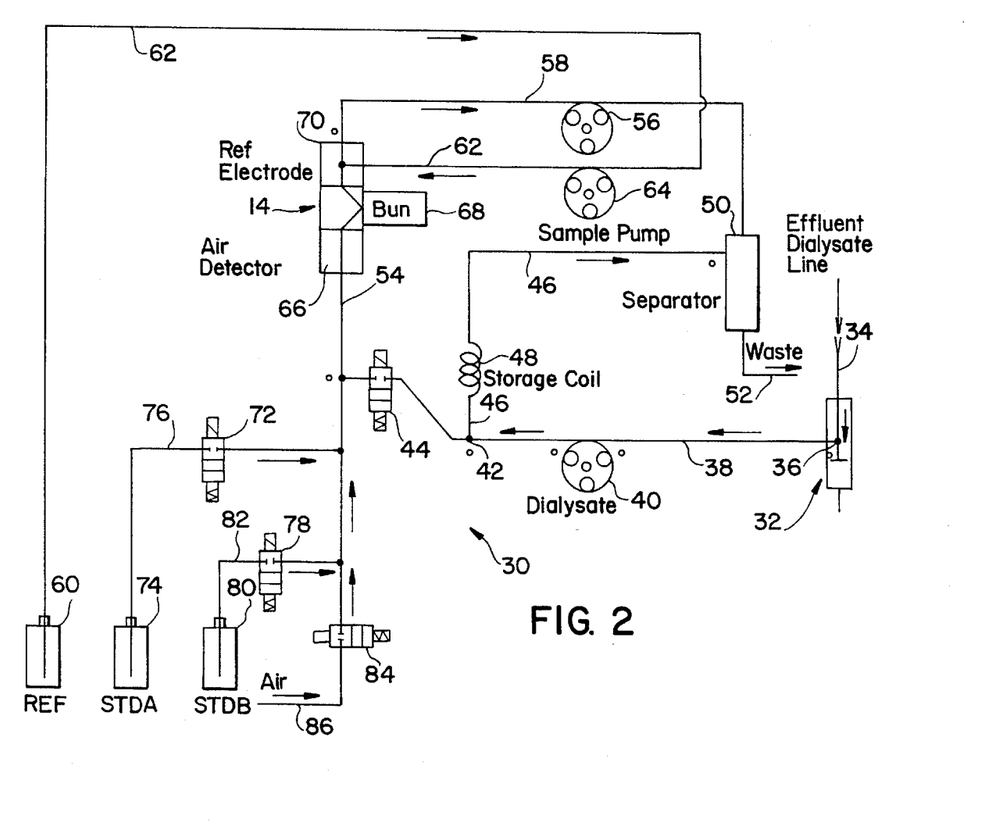
FIG. 2 is a schematic diagram of one embodiment of a portion of the hemodialysis monitoring system of FIG. 1.

One urea input/sensor module embodiment of the urea input module 12 and the urea sensor 14 of the hemodialysis monitoring system 10 of the present invention is designated generally by the reference numeral 30 in FIG. 2. The module 30 includes a sample port 32, which preferably forms a part of a discharge or dialysate effluent line 34. The module 30 taps into the dialysate effluent line 34 via a junction 36 coupled to a sampling line 38.

The module 30 samples the dialysate effluent by activating a self occluding peristaltic or roller pump 40. The line 38 is coupled to a junction 42 and to a normally closed valve 44. The junction 42 also is coupled to a line 46, which includes a storage coil 48. The storage coil 48 is first filled with the dialysate effluent, with the excess dialysate effluent continuing through the line 46 to a separator 50. The separator 50 includes an air gap, which prevents a backup of the dialysate effluent and also prevents an electrical short through the line 52.

Once the storage coil 48 is filled, the pump 40 is stopped, which closes the line 38 from the junction 36. The valve 44 then is opened allowing the sample dialysate to flow through the valve into a line 54 and then to and past the urea sensor 14. The sample dialysate is caused to flow by a sample pump 56, which is coupled between the urea sensor 14 and the discharge separator 50 by a line 58.

For each measurement, sample dialysate preferably is input to the urea sensor 14 and flushed through the separator 50 several times to ensure a good sample value. At the same time the sample dialysate is pumped through the urea sensor 14, a reference fluid from a source 60 also is pumped into the urea sensor 14 via a line 62 and a second pump 64. The second pump 64 preferably can be a second roller head on the sample pump 56, but could also be a second pump coupled to operate at the same time as the sample pump 56.

As shown in more detail in U.S. Pat. No. 4,686,479, the urea sensor 14 includes an air detector 66 to determine if the sample dialysate is present in the urea sensor 14. The sensor 14 employs an electrode 68 with a membrane (not illustrated) which is specific to ammonium. The electrode 68 senses dialysate urea nitrogen (DUN) which is compared to a reference electrode 70. The signal generated by the sensor 14 then is coupled to the signal analyzer 18, as will be described in more detail hereinafter.

At the beginning of the hemodialysis treatment with a patient and periodically as desired, both a low reference standard and a high reference standard are run on the module 30 to calibrate the module 30. To calibrate the module 30 with the low standard, the valve 44 remains closed and a valve 72 is opened to allow the second pump 64 to draw in the low standard fluid from a source 74 via a line 76. The urea sensor 14 measures the low standard, which is compared to an expected range of values to ensure that the urea sensor 14 is calibrated correctly. The low standard also can be utilized to test the integrity of the system during treatment.

A similar operation is performed with a high reference standard. To run a high standard test, all the valves are closed, except for a high standard valve 78. The open valve 78 allows the second pump 64 to draw a high standard fluid from a source 80 via a line 82. The high standard fluid is measured in the urea sensor 14 and compared to an expected range of values to ensure that the urea sensor also is operating correctly at the high standard range.

At the end of the low standard cycle testing, the module 30 closes the valves 44, 72 and 78 and opens an air valve 84 for a period of time, which allows the sample pump 64 to draw air into a line 86 through the valve 84, the urea sensor 14 and out the discharge line 52. This air segment between each fluid segment helps ensure that the urea sensor 14 and the lines 54 and 58 are clean and empty of any substantial amount of residual fluid.

Figure 3:
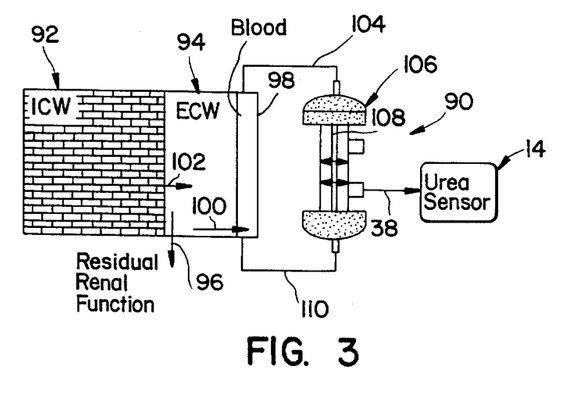
FIG. 3 is a partial block and partial schematic diagram of the fluid functions of the hemodialysis monitoring system.

Referring now to FIG. 3, a schematic embodiment of the operation of the hemodialysis monitoring system 10 of the present invention is designated generally by the reference character 90. The system 90 is depicted diagrammatically as including an intracellular space (ICW) 92 and an extracellular space (ECW) 94, which spaces are representative of the body pools in a hemodialysis patient. The hemodialysis kinetic parameters in the system 90 are calculated from the spent dialysate of a patient undergoing a typical dialysis treatment. The urea is generated in the liver, which is illustrated as being a portion of the ECW 94.

Some of the urea may be removed by the patient's kidneys, if there is a residual renal function, as indicated by an arrow 96. The majority of the urea, however, is removed by the hemodialysis treatment after first contacting the blood 98 in the ECW 94, as indicated by an arrow 100. Urea also enters the ECW 94 from the ICW 92, as indicated by an arrow 102.

The blood is removed during the hemodialysis treatment by flowing through a line 104 into a dialysis cartridge 106.

The dialysis cartridge 106 diagrammatically includes a dialyzer membrane 108 across which urea diffuses into the dialysate. A sample volume of the dialysis effluent is removed through the line 38 and then is sensed by the urea sensor 14, as above described. The blood returns to the patient via a line 110.

In a steady state condition, the total amount of urea removed during the hemodialysis treatment and sensed by the urea sensor 14 is equal to the rate of generation of urea in the patient's body in ECW 94. This allows the calculation of the normalized protein catabolic rate (nPCR) or the number of grams of urea generated per kilogram of body mass in a twenty-four hour period. Further, by knowing the concentration-time profile of urea, inferences can be made about the clearance of the dialyzer cartridge 106 and the clearance-time/body water index (KT/V) which is a measure of dialysis adequacy then can be calculated.

Figure 4:
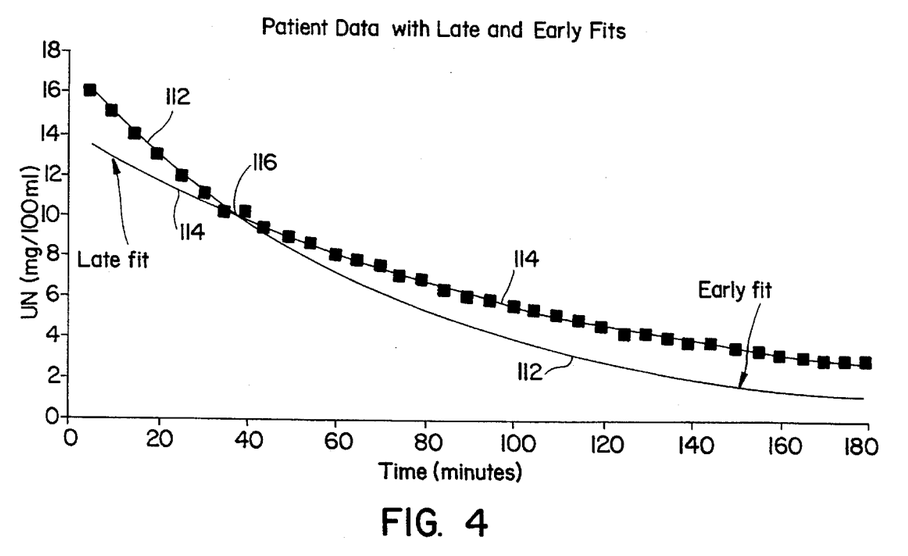
FIG. 4 is a urea concentration time profile of a typical patient illustrating a two pool analysis of the patient.

FIG. 4 illustrates a urea concentration-time profile of a typical patient as detected by the urea sensor 14. Applicants have discovered that the urea concentration-time profile can be closely matched to an early fit exponential curve 112 and to a late fit exponential curve 114. The two curves 112 and 114 are exponential fits of the urea concentration data pre and post thirty (30) minutes into the hemodialysis treatment. An empirically determined "inflection" point 116 is indicative of the difference in the fits 112 and 114, which is a gradual shift caused by the two-pool nature of the urea removal from the patient's ICW 92 and ECW 94.

Initially in the hemodialysis treatment, the system 90 removes urea quite rapidly from the patient's blood and from the ECW 94 with which the blood 98 is in intimate contact. Thus, the initial fit 112, before the point 116 is a fairly steep slope. After a period of time, approximately thirty (30) minutes, enough urea is removed from the ECW 94 to create a urea gradient between the ICW 92 and the ECW 94.

At the point 116, the rate of urea removal from the ECW 94 decreases and the rate of urea removal from the cells in the ICW 92 increases. The latter is a result of a growing concentration differential between the ECW 94 and the ICW 92. The removal of urea from the patient's body is dependent upon the intercompartmental mass transfer area coefficient (iMTAC) (which controls mass transfer between the ICW 92 and ECW 94) and the dialyzer mass transfer area coefficient (dMTAC)(which controls the mass transfer between the ECW 94 and the dialysate flow). The iMTAC is typically smaller than the dMTAC which causes the concentration differential between the ECW 94 and ICW 92. Consequently the fit 114 after the point 116 has a more flat slope, than the slope of the early fit 112. It thus is clear that a single pool analysis is much less accurate than the two pool behavior as determined by the present invention.

Figure 5:
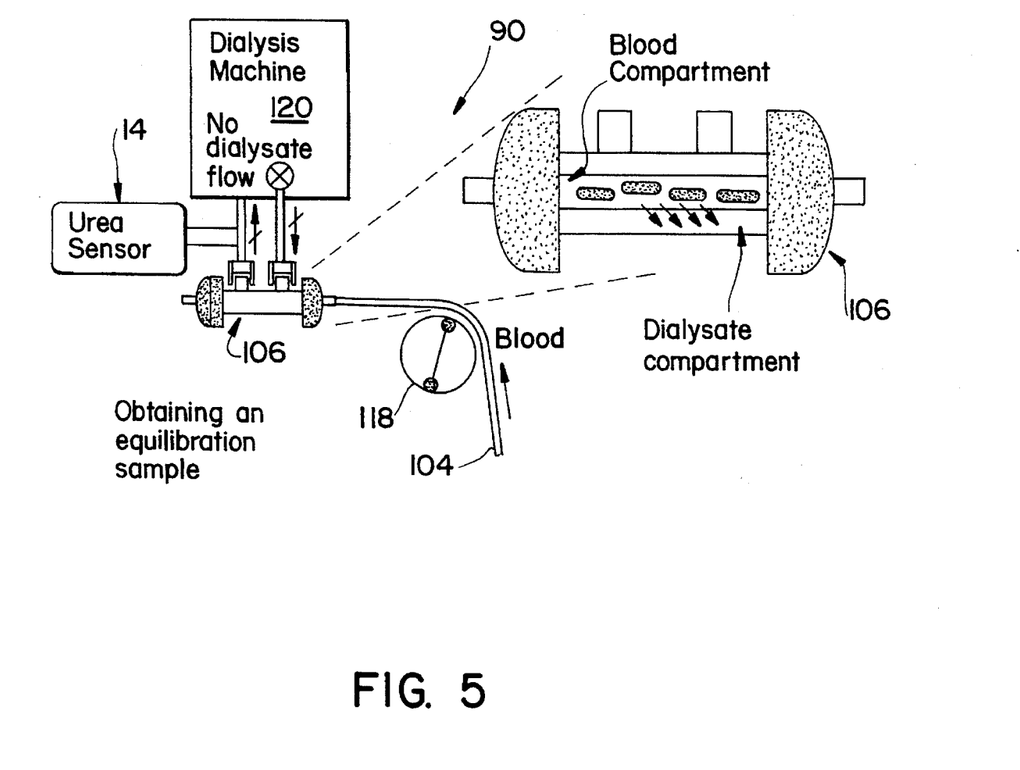
FIG. 5 is a functional block diagram illustrating the equilibration of the hemodialysis monitoring system.

The calculation of KT/V, URR and SRI employing the two pool analysis in accordance with either of the systems 10 or 30 is as follows. In one preferred embodiment, prior to initiating the hemodialysis treatment, the hemodialysis monitoring system 10 or 30 of the present invention, for example purposes, is equilibrated with the patient's blood as illustrated in FIG. 5. The blood is pumped to the dialysis cartridge 106 via the line 104, such as by a roller pump 118. The dialysis cartridge 106 is connected to and forms a portion of a conventional dialysis machine 120.

To obtain the equilibrated urea sample analysis, after initial filling of the dialyzer with dialysate, the dialysate flow is shunted past the dialysis cartridge 106 or stopped, while the blood is pumped through the dialysis cartridge 106. No dialysate flow is allowed between the dialysis cartridge 106 and the dialysis machine 120, however ultrafiltration does exist even with the dialysate flow in bypass. After an elapsed time period, such as five (5) minutes, during which the urea concentrations of the blood and the dialysate are allowed to equilibrate across the membrane, an equilibration sample is obtained and sensed by the urea sensor 14. The equilibration sample provides the urea concentration in the patient's blood before the dialysis treatment. The equilibrated concentration is utilized in conjunction with the dialyzer typical profiles, dialysate clearance (K) and total body water (V) to calculate KT/V, URR, nPCR, and the solute removal index (SRI).

Figure 6:
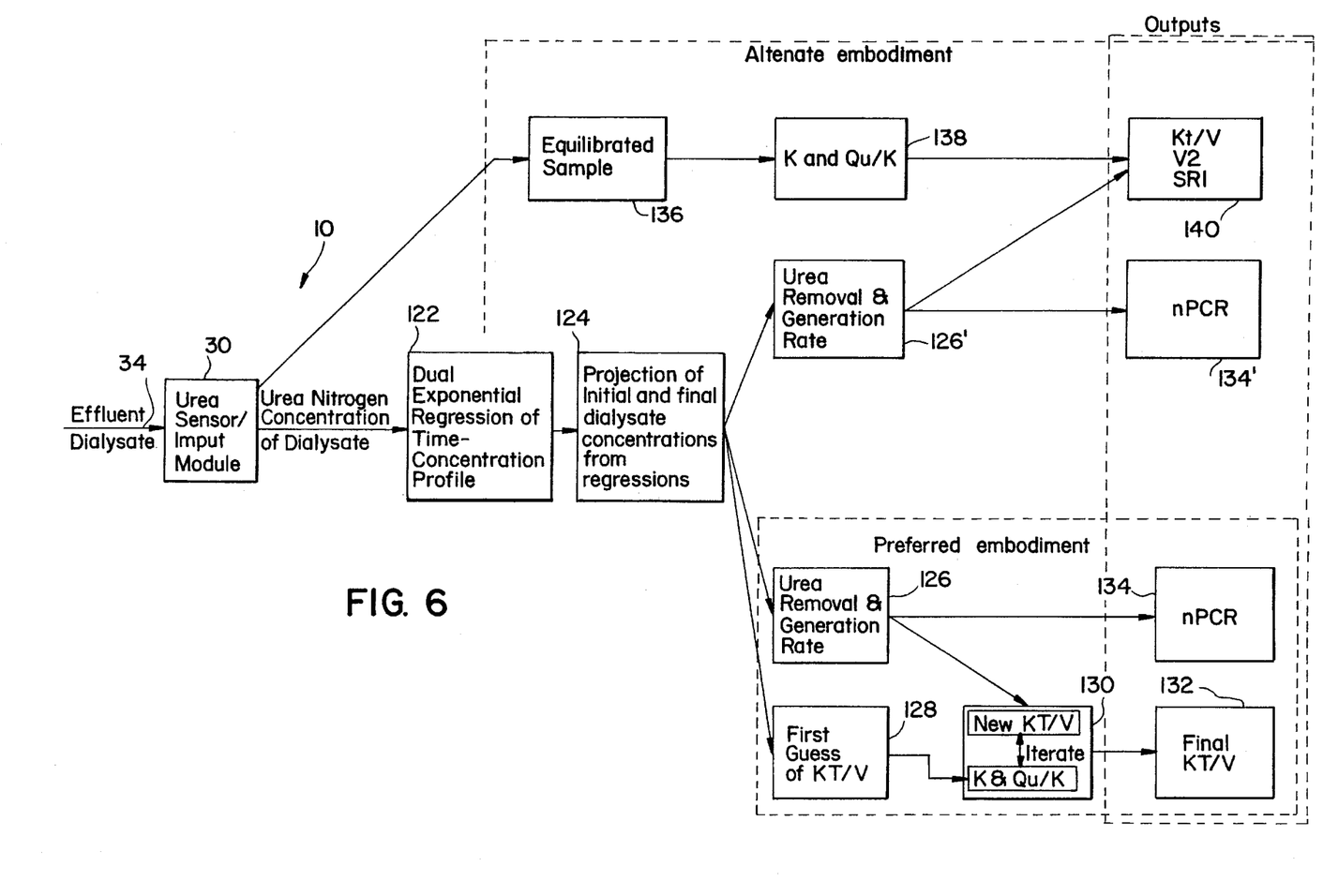
FIG. 6 is a flow chart of the preferred embodiments of the present invention.

Utilizing a first preferred embodiment of the hemodialysis monitoring system 10, without obtaining an equilibrated sample, the following steps are performed, as illustrated in FIG. 6:

1. Two exponential regressions of the concentration/time profile are performed, with the first regression fit covering the segment from zero to thirty (0–30) minutes, and the second regression fit covering the segment from thirty (30) minutes to the current time as indicated by block 122.

2. The initial ($CD_1$), thirty (30) minute ($CD_{30}$), current minute ($CD_t$), and final ($CD_2$) dialysate urea concentrations are projected from these regressions and the log mean dialysate concentration is calculated for each segment as indicated by block 124.

3. Urea removal for each segment then is calculated as the product of log mean dialysate concentrations, dialysate outflow (QDo) and segment time. These products are summed to obtain the projected urea removal (R) for the dialysis treatment as indicated by block 126.

4. Because of the typical unequal spacing of dialysis treatments over a seven (7) day period, urea removal for a given treatment is dependent upon the day of the week. A factor (F) was derived from a variable volume urea kinetic model utilizing a range of clearances (K), urea distribution volumes (V), urea generation rates (G), ultrafiltration rates ($Q_u$), and treatment times (T). The projected weekly removal ($R_{wk}$) is calculated using F and R.

5. G (in mg/minute) then is calculated from $R_{wk}$.

6. $Q_u$ is calculated from total ultrafiltration and treatment time.

7. A "first guess" (estimate) for KT/V is calculated utilizing the formula $(KT/V)_{fg} = LN(CD_1/CD_2)$, with $CD_1$ and $CD_2$ projected from the exponential regressions of the time/concentration profile as indicated by block 128.

8. K and $Q_u/K$ are calculated from $(KT/V)_{fg}$ and an estimate of V (as percentage of body weight; 51% for males, 43% for females).

9. $Q_u T/V$ and hence a new KT/V are calculated as indicated by block 130 utilizing the formula:

$$LN\left[1 + \frac{Q_u*T}{V}\right] = \frac{Q_u}{(K-Q_u)} * LN\left[\frac{\left(CD_1 - \frac{G}{K-Q_u}\right)}{\left(CD_2 - \frac{G}{K-Q_u}\right)}\right]$$

10. A new K is calculated from the KT/V obtained in step 9.

11. Iteration of steps 9–10 is continued until convergence is obtained which results in a final KT/V as indicated by block 132.

12. The normalized protein catabolic rate (nPCR) then is calculated utilizing G and V as indicated by block 134.

13. In lieu of KT/V, URR can also be reported as $1-CD_1/CD_2$.

Utilizing a second preferred embodiment of the hemodialysis monitoring system 10, after first obtaining an equilibrated sample, the following steps are performed, as also illustrated in FIG. 6:

The dialysate sample has been equilibrated with blood before the dialysis treatment ($Cb_{equil}$) (as described elsewhere) as indicated by block 136:

1. Steps 1–6 are performed as above.
2. Clearance (K) is calculated directly from $Cb_{equil}$, QDo and $CD_1$ as indicated by block 138.
3. KT/V is calculated utilizing the formula in step 9 above as indicated by block 140.
4. Kinetic volume of urea distribution ($V_2$) is calculated from KT/V (step 3) as indicated by a block 126' and K (step 2) as indicated by block 138.
5. Solute Reduction Index (SRI) represents the fraction of solute (urea) that has been removed from the total body stores by hemodialysis and is calculated as indicated by block 140 from:

$$SRI=[R-G*T(\text{dialysis})]/(V_1*Cb_{equil})$$

where $V_1=V_2+\text{ultrafiltration}$.

11. The normalized protein catabolic rate (nPCR) then is calculated utilizing G and V as before as indicated by block 134'.
12. In lieu of KT/V, URR can also be reported as $1-CD_1/CD_2$.

The first embodiment can be utilized where the system 10 is not an integral portion of a hemodialysis machine, since the equilibrated sample then must be obtained by an operator in a manual mode of operation. The second embodiment preferably can be utilized when the system 10 is integrated with or is able to automatically control the hemodialysis machine to automatically obtain the equilibrated sample without operator intervention.

As further embodiments:

1. The concentration/time profile also could be fit with a single exponential regression to project $CD_1$, $CD_2$, and R.
2. The concentration/time profile could be fit with a non-linear regression (e.g. the sum of two exponentials). The exponents resulting from these regressions then would be utilized to calculate K, G, and V utilizing standard two-pool urea kinetics determined for blood urea concentration/time profiles.
3. Also, a percent urea reduction method utilized for blood urea concentrations (e.g. a formula of the type: KT/V= –LN[Cpost/Cpre- 008*Time—Ultrafiltration/Weight]) could be utilized to calculate KT/V utilizing dialysate urea concentrations.

In the further embodiments, number 1 and 3 result in a KT/V that represents single-pool urea kinetics, while the preferred embodiments, previously described and the further embodiment number 2, result in a KT/V that represents two-pool urea kinetics.

The hemodialysis monitoring system 10 can draw a sample volume at any predetermined time period. It empirically has been determined that a time period on the order of every ten (10) minutes is sufficient for the hemodialysis treatment, since the urea concentration values change at a relatively slow rate. The rate change is sufficiently slow, such that continuous sampling is not required and intermittent sampling is sufficiently accurate to represent real time.

Thus, sampling the dialysis effluent every five (5) to ten (10) minute period provides a real time urea concentration profile. A convenient sample volume, utilizing the urea sensor 14 is on the order of two (2) milliliters (ml) of dialysate effluent. The hemodialysis monitoring system 10 can also provide an equilibrated urea concentration value at the end of the hemodialysis treatment.

Because of the technique of the hemodialysis monitoring system 10 of the present invention, after about sixty (60) to ninety (90) minutes of a three (3) to four (4) hour hemodialysis treatment, the final urea concentration value can be projected. This mid-treatment projection then can be utilized to trouble shoot the hemodialysis treatment, if the final projected KT/V result is too low.

In a typical patient, when the hemodialysis treatment is initialized, the patient's blood will contain on the order of seventy (70) milligrams (mg) of urea in one hundred (100) ml of blood. After four (4) hours of the hemodialysis treatment, the patient's blood will contain on the order of thirty (30) mg of urea in one hundred (100) ml of blood. On the dialysate side of the dialysate cartridge 106, the dialysate after initiating treatment initially will contain on the order of twenty-five (25) mg of urea in one hundred (100) ml of dialysate. After the four (4) hours of the hemodialysis treatment, the dialysate will contain on the order of five (5) to seven (7) mg of urea in one hundred (100) ml of dialysate, since the clearance decreases during the hemodialysis treatment.

The urea change is exponential, such that about one half of the urea is removed in about one third of the total hemodialysis treatment time period. Since the urea change is exponential, it is convenient to sample more frequently in the initial part of the hemodialysis treatment time period. For example during a four (4) hour hemodialysis treatment, the hemodialysis monitoring system 10 can be set to sample every five (5) minutes in the first hour and then every ten (10) minutes during the rest of the hemodialysis treatment.

Applicants empirically have determined that the two pool analysis of the hemodialysis monitoring system 10, as described with respect to FIG. 4, is on the order of twelve (12) to eighteen (18) percent more accurate, than the conventional one pool analyses. The hemodialysis monitoring system 10 also is set to monitor the dialysis effluent, only when the hemodialysis machine 120 is operating. Some prior art systems utilize a total clock period, without regard to dialysis shut down periods due to system alarms.

Further, as is described in more detail in the above cross-referenced application, for a Fluid Sampling Module, the hemodialysis monitoring system 10 is prevented from sampling the dialysate effluent during a period of no or very low dialysate effluent flow. Sampling during a period of no or unstable flow, also can introduce errors into the analysis treatment. Urea is a convenient marker to utilize in the hemodialysis treatment, since it is related to other uremic toxin levels, but other well known markers also can be utilized in the hemodialysis treatment of the present invention as previously described.

The prior art hemodialysis monitoring treatment typically draws a blood sample from the patient (an invasive treatment), typically on the order of once a month. The urea concentration value then is utilized as the initial hemodialysis treatment value. The final or post hemodialysis treatment value is obtained from a blood sample taken after the end of the hemodialysis treatment. The urea concentration ratio from these two blood samples then is utilized to determine the efficiency of the hemodialysis treatment, which provides a KT/V value which is not as accurate as that obtained utilizing the present invention.

The prior art analysis is further inaccurate, because although the urea concentration in the ICW 92 attempts to equalize with that in the ECW 94, there is a considerable time lag. The urea is removed rapidly from the blood, resulting in a significant differential between the urea concentration in the ICW 92 and in the ECW 94 at the end of the hemodialysis treatment. At the end of a typical hemodialysis treatment, urea concentrations can be about forty (40) mg/dl in the ICW 92 and about thirty (30) mg/dl in the ECW 94. Thus, since the ICW 92 has a total nominal volume greater than the ECW 94 total nominal volume, the final ECW 94 urea concentration value of about thirty (30) mg/dl can be very inaccurate. The single or one pool analysis does not take into account the difference between the final urea concentration in the ICW 92 and the ECW 94. Since the one pool analysis generally is based upon the urea concentration in the ECW 94, if an equalization or rebound period on the order of thirty (30) to sixty (60) minutes is not accounted for, the analysis will overestimate the true KT/V. Continued diffusion from the ICW 92 into the ECW 94 causes the concentration of the ECW 94 to rebound or increase with time.

The hemodialysis monitoring system 10 is described as a separate unit, which is attached to the lines of the dialysis cartridge 106, which is pan of the dialysis machine 120. The hemodialysis monitoring system 10 also can be retrofit to the dialysis machine 120 or can be fully integrated into the dialysis machine 120 without departing from the spirit or scope of the present invention.

We claim as our invention:

1. A method of monitoring a hemodialysis treatment in real time for utilization with a hemodialysis machine including a dialyzer and with dialysate waste effluent removed from the dialyzer, comprising:

providing a dialysate effluent constituent sensor and separately coupling a plurality of separate fluid portions of the dialysate effluent to said constituent sensor during a dialysis treatment;

detecting and measuring concentrations of said constituent in each of said dialysate effluent portions;

determining a dialysate constituent concentration-time profile from said dialysate constituent concentration measurements;

forming at least a two pool analysis to account for the differences in the constituent concentration in the extracellular and the intracellular spaces in a patient during the dialysis treatment; and directly determining an indication of adequacy of said dialysis treatment from said dialysate constituent concentration-time profile.

2. The method as defined in claim 1 including said constituent being related to urea and providing a urea sensor to determine a urea concentration-time profile and determining at least one of urea removal, KT/V, PCR and URR from said urea concentration-time profile.

3. The method as defined in claim 2 including obtaining an equilibrated urea concentration measurement prior to starting the dialysis treatment and determining a solute removal index (SRI) from said equilibrated concentration measurement and said urea concentration-time profile.

4. The method as defined in claim 2 including obtaining an equilibrated urea concentration measurement after completing the dialysis treatment and determining a solute removal index (SRI) from said equilibrated concentration measurement and said urea concentration-time profile.

5. The method as defined in claim 2 including projecting a final urea concentration value for the completion of the dialysis treatment from said urea concentration-time profile at a point in time significantly prior to completing said dialysis treatment and projecting at least one of urea removal, KT/V, URR, PCR and a solute removal index (SRI) from said projected final urea concentration value.

6. The method as defined in claim 2 including calculating at least one of KT/V, PCR and URR from said two pool analysis.

7. The method as defined in claim 6 including forming two separate exponential fits of said urea concentration measurements to determine said urea concentration-time profile.

8. The method as defined in claim 6 including fitting said urea concentration measurements to a nonlinear function to describe said urea concentration-time profile.

9. The method as defined in claim 6 including obtaining an equilibrated urea concentration measurement prior to starting the dialysis treatment and determining a solute removal index (SRI) from said equilibrated concentration measurement and said urea concentration-time profile.

10. The method as defined in claim 6 including obtaining an equilibrated urea concentration measurement after completing the dialysis treatment and determining a solute removal index (SRI) from said equilibrated concentration measurement and said urea concentration-time profile.

11. The method as defined in claim 6 including projecting at least one of a final urea concentration value, final urea removal, final KT/V, final PCR, final URR and a final solute removal index (SRI) for the completion of the dialysis treatment from said urea concentration-time profile at a point in time significantly prior to completing said dialysis treatment.

12. The method as defined in claim 1 wherein said dialysate constituent time concentration profile is utilized for conducting a protein assessment.

13. An apparatus adapted for monitoring a hemodialysis treatment in real time for utilization with a hemodialysis machine including a dialyzer and with dialysate waste effluent removed from the dialyzer, comprising:

a dialysate effluent constituent sensor and means for separately coupling a plurality of separate fluid portions of the dialysate effluent to said constituent sensor during a dialysis treatment;

means for detecting and measuring concentrations of said constituent in each of said dialysate effluent portions;

means for determining a constituent concentration-time profile from said dialysate constituent concentration measurements;

means for forming at least a two pool analysis to account for the differences in the constituent concentration in the extracellular and the intracellular spaces in a patient during the dialysis treatment; and means for directly determining an indication of adequacy of said dialysis treatment from said dialysate constituent concentration-time profile.

14. The apparatus as defined in claim 13 including said constituent being related to urea and including a urea sensor to determine a urea concentration-time profile and means for determining at least one of urea removal, KT/V, PCR and URR from said urea concentration-time profile.

15. The apparatus as defined in claim 14 including means for obtaining an equilibrated urea concentration measurement prior to starting the dialysis treatment and means for determining a solute removal index (SRI) from said equilibrated concentration measurement and said urea concentration-time profile.

16. The apparatus as defined in claim 14 including means for obtaining an equilibrated urea concentration measurement after completing the dialysis treatment and means for determining a solute removal index (SRI) from said equilibrated concentration measurement and said urea concentration-time profile.

17. The apparatus as defined in claim 14 including means for projecting a final urea concentration measurement for the completion of the dialysis treatment from said urea concentration-time profile at a point in time significantly prior to completing said dialysis treatment and projecting at least one of urea removal, KT/V, URR, PCR and a solute removal index (SRI) from said projected final urea concentration value.

18. The apparatus as defined in claim 14 including means for calculating at least one of KT/V, PCR and URR from said two pool analysis.

19. The apparatus as defined in claim 18 including means for forming two separate exponential fits of said urea concentration measurements to determine said urea concentration-time profile.

20. The apparatus as defined in claim 18 including means for fitting said urea concentration measurements to a nonlinear function to describe said urea concentration-time profile.

21. The apparatus as defined in claim 18 including means for obtaining an equilibrated urea concentration measurement prior to starting the dialysis treatment and means for determining a solute removal index (SRI) from said equilibrated concentration measurement and said urea concentration-time profile.

22. The apparatus as defined in claim 18 including means for obtaining an equilibrated urea concentration measurement after completing the dialysis treatment and means for determining a solute removal index (SRI) from said equilibrated concentration measurement and said urea concentration-time profile.

23. The apparatus as defined in claim 18 including means for projecting at least one of a final urea concentration value, final urea removal, final KT/V, final PCR, final URR and a final solute removal index (SRI) for the completion of the dialysis treatment from said urea concentration-time profile at a point in time significantly prior to completing said dialysis treatment.

24. The apparatus as defined in claim 13 further comprising means for conducting protein assessment from the dialysate constituent time concentration profile.

25. A method of monitoring a hemodialysis treatment in real time for utilization with a hemodialysis machine including a dialyzer and with dialysate waste effluent removed from the dialyzer, comprising:
providing a dialysate effluent urea sensor and separately coupling a plurality of separate fluid portions of the dialysate effluent to said urea sensor during a dialysis treatment;
detecting and measuring concentrations of said urea in each of said dialysate effluent portions;
determining a dialysate urea concentration-time profile from said dialysate urea concentration measurements;
forming at least a two pool analysis to account for the differences in the urea concentration in the extracellular and the intracellular spaces in a patient during the dialysis treatment; and
directly determining an indication of adequacy of said dialysis treatment from said dialysate urea concentration-time profile.

26. The method as defined in claim 25 including determining at least one of urea removal, KT/V, URR and PCR from said urea concentration-time profile.

27. The method as defined in claim 25 including obtaining an equilibrated urea concentration measurement prior to starting the dialysis treatment and determining a solute removal index (SRI) from said equilibrated concentration measurement and said urea concentration-time profile.

28. The method as defined in claim 25 including obtaining an equilibrated urea concentration measurement after completing the dialysis treatment and determining a solute removal index (SRI) from said equilibrated concentration measurement and said urea concentration-time profile.

29. The method as defined in claim 25 including projecting a final urea concentration value for the completion of the dialysis treatment from said urea concentration-time profile at a point in time significantly prior to completing said dialysis treatment and projecting at least one of urea removal, KT/V, URR, PCR and a solute removal index (SRI) from said projected final urea concentration value.

30. The method as defined in claim 25 including calculating at least one of KT/V, PCR and URR from said two pool analysis.

31. The method as defined in claim 30 including forming two separate exponential fits of said urea concentration measurements to determine said urea concentration-time profile.

32. The method as defined in claim 30 including fitting said urea concentration measurements to a nonlinear function to describe said urea concentration-time profile.

33. The method as defined in claim 30 including obtaining an equilibrated urea concentration measurement prior to starting the dialysis treatment and determining a solute removal index (SRI) from said equilibrated concentration measurement and said urea concentration-time profile.

34. The method as defined in claim 30 including obtaining an equilibrated urea concentration measurement after completing the dialysis treatment and determining a solute removal index (SRI) from said equilibrated concentration measurement and said urea concentration-time profile.

35. The method as defined in claim 30 including projecting at least one of a final urea concentration value, final urea removal, final KT/V, final PCR, final URR and a final solute removal index (SRI) for the completion of the dialysis treatment from said urea concentration-time profile at a point in time significantly prior to completing said dialysis treatment.

36. The method as defined in claim 25 wherein said dialysate urea time concentration profile is utilized for conducting a protein assessment.

37. An apparatus adapted for monitoring a hemodialysis treatment in real time for utilization with a hemodialysis machine including a dialyzer and with dialysate waste effluent removed from the dialyzer, comprising:
a dialysate effluent urea sensor and means for separately coupling a plurality of separate fluid portions of the dialysate effluent to said urea sensor during a dialysis treatment;
means for detecting and measuring concentrations of said urea in each of said dialysate effluent portions;
means for determining a urea concentration-time profile from said dialysate urea concentration measurements;
means for forming at least a two pool analysis to account for the differences in the urea concentration in the extracellular and the intracellular spaces in a patient during the dialysis treatment; and
means for directly determining an indication of adequacy of said dialysis treatment from said urea dialysate concentration-time profile.

38. The apparatus as defined in claim 37 including said constituent being related to urea and including a urea sensor to determine a urea concentration-time profile and means for determining at least one of urea removal, KT/V, PCR and URR from said urea concentration-time profile.

39. The apparatus as defined in claim 37 including means for obtaining an equilibrated urea concentration measurement prior to starting the dialysis treatment and means for determining a solute removal index (SRI) from said equilibrated concentration measurement and said urea concentration-time profile.

40. The apparatus as defined in claim 37 including means for obtaining an equilibrated urea concentration measurement after completing the dialysis treatment and means for determining a solute removal index (SRI) from said equilibrated concentration measurement and said urea concentration-time profile.

41. The apparatus as defined in claim 37 including means for projecting a final urea concentration measurement for the completion of the dialysis treatment from said urea concentration-time profile at a point in time significantly prior to completing said dialysis treatment and projecting at least one of urea removal, KT/V, URR, PCR and a solute removal index (SRI) from said projected final urea concentration value.

42. The apparatus as defined in claim 34 including means for calculating at least one of KT/V, PCR and URR from said two pool analysis.

43. The apparatus as defined in claim 42 including means for forming two separate exponential fits of said urea concentration measurements to determine said urea concentration-time profile.

44. The apparatus as defined in claim 42 including means for fitting said urea concentration measurements to a non-linear function to describe said urea concentration-time profile.

45. The apparatus as defined in claim 42 including means for obtaining an equilibrated urea concentration measurement prior to starting the dialysis treatment and means for determining a solute removal index (SRI) from said equilibrated concentration measurement and said urea concentration-time profile.

46. The apparatus as defined in claim 42 including means for obtaining an equilibrated urea concentration measurement after completing the dialysis treatment and means for determining a solute removal index (SRI) from said equilibrated concentration measurement and said urea concentration-time profile.

47. The apparatus as defined in claim 42 including means for at least one of a final urea concentration value, final urea removal, final KT/V, final PCR, final URR and a final solute removal index (SRI) for the completion of the dialysis treatment from said urea concentration-time profile at a point in time significantly prior to completing said dialysis treatment.

48. The apparatus as defined in claim 37 further comprising means for conducting protein assessment from the dialysate urea time concentration profile.

* * * * *

UNITED STATES PATENT AND TRADEMARK OFFICE
CERTIFICATE OF CORRECTION

PATENT NO. : 5,518,623

DATED : May 21, 1996

INVENTOR(S) : Prakash Keshaviah, et. al.

It is certified that error appears in the above-identified patent and that said Letters Patent is hereby corrected as shown below:

Column 1, Line 24:   delete "carded" and insert —carried—

Column 3, Line 12:   delete "at." and insert —al.—

Column 8, Line 19:   delete "coveting" and insert —covering—

Column 14, Line 7:   delete "SRD" and insert —SRI—

Signed and Sealed this

First Day of October, 1996

Attest:

BRUCE LEHMAN

Attesting Officer        Commissioner of Patents and Trademarks